United States Patent
Bell et al.

(10) Patent No.: US 6,695,807 B2
(45) Date of Patent: Feb. 24, 2004

(54) BLOOD FLOW REVERSING SYSTEM

(75) Inventors: David Bell, Grayslake, IL (US); William J. Schnell, Libertyville, IL (US); David S. Utterberg, Seattle, WA (US)

(73) Assignee: DSU Medical, Inc., Las Vegas, NV (US)

( * ) Notice: Subject to any disclaimer, the term of this patent is extended or adjusted under 35 U.S.C. 154(b) by 0 days.

(21) Appl. No.: 10/051,465

(22) Filed: Jan. 18, 2002

(65) Prior Publication Data

US 2003/0138348 A1 Jul. 24, 2003

(51) Int. Cl.$^7$ .................. A61M 37/00; A61M 1/36; C02F 1/44
(52) U.S. Cl. .............. 604/6.16; 604/4.01; 604/6.1; 422/44; 210/646
(58) Field of Search .................. 604/4.01, 5.01, 604/6.1, 6.16, 27–32, 34, 507–8, 167.01, 167.05, 178, 247, 250, 523, 533–35, 537–38, 284; 422/44, 61; 210/645, 767, 782; 128/DIG. 3, 898; 251/4, 12; 138/118; 137/109, 825, 829, 832, 561 R, 561 A, 565.01, 614

(56) References Cited

U.S. PATENT DOCUMENTS

| | | | |
|---|---|---|---|
| 4,820,265 A | * | 4/1989 | DeSatnick et al. ............ 604/30 |
| 4,885,087 A | | 12/1989 | Kopf |
| 5,454,374 A | | 10/1995 | Omachi |
| 5,830,365 A | | 11/1998 | Schneditz |
| 5,894,011 A | | 4/1999 | Prosl et al. |
| 6,177,049 B1 | | 1/2001 | Schnell et al. |
| 6,308,737 B1 | | 10/2001 | Krivitski |
| 6,319,465 B1 | | 11/2001 | Schnell et al. |
| 6,572,576 B2 | | 6/2003 | Brugger et al. |

* cited by examiner

*Primary Examiner*—Patricia Bianco
(74) *Attorney, Agent, or Firm*—Garrettson Ellis Seyfarth Shaw LLP

(57) ABSTRACT

A tubular set portion for circulating blood between a patient and an extracorporeal blood treatment device. The set portion has: an arterial tube for conveying blood from a patient toward the blood treatment device; a venous tube for conveying blood from the blood treatment device back towards the patient; and a pair of spaced, transverse tubes that each connect between the arterial tube and the venous tube, each of the tubes being capable of clamp sealing. The arterial and venous tubes are clamp sealable between the spaced, transverse tubes. Flow reversal on the patient's side of this device is possible by appropriate clamping of two opposed tube sections of the rectangular array which may be formed by the joined tube sections, while flow remains unchanged on the side of the tubular set portion that is connected to the extracorporeal blood treatment device.

38 Claims, 5 Drawing Sheets

BLOOD FLOW REVERSING SYSTEM

BACKGROUND OF THE INVENTION

As discussed in Schnell, et al., U.S. Pat. No. 6,319,465 and elsewhere, hemodialysis and other forms of extracorporeal blood treatment require the removal of blood from a patient by means of an arterial tube set, the passing of the blood to a blood processing device such as a dialyzer, and the subsequent returning of the blood to the patient again through a venous tube set.

Maintenance of good blood set access is a major cost and problem of dialysis, which is the most common extracorporeal blood treatment, although other types of blood treatment are also known, for example, passing of the blood through an absorption bed for removal of toxins or the like, hemoperfusion, and other forms of blood treatment.

Beyond the initial cost of the surgical procedure to establish a fistula or graft in the patient, the keeping of adequate blood flow in an arterialized vein or synthetic arteriovenous graft of the patient frequently involves secondary surgical intervention for reconstruction of an old blood vessel site on the patient. Alternatively, it may be necessary to establish an entirely new fistula or graft at a new site if the old one fails.

Such failure is evidenced typically by stenosis of the blood vessel, or blockage of an implanted catheter or other venous access site, with a consequent reduction in blood flow that eventually shuts down the site. Clotting is also a major cause of reduced blood flow.

If site failure is detected early enough, a less invasive technique such as balloon angioplasty can be employed to open the stenosis at a greatly reduced cost. Early detection of stenosis can be measured by a change in pressure in the blood vessel or implant that reflects a restriction beginning to form. The technique described in Omachi, U.S. Pat. No. 5,454,374, has been used to measure the baseline pressure access site for early detection of such a pressure change. Another method used by clinicians is to measure recirculation in the vessel during dialysis. As the flow is restricted in the access, the blood pumping rate indicated on the dialysis machine may exceed the flow rate of fresh blood coming into the vessel, so that some is recirculated from the venous access site to the arterial access site in the patient. This leads to inadequate dialysis since already cleansed blood is thus being reprocessed.

Various methods for measuring the degree of this recirculation are known. A method described by Krivitski determines blood flow in the access as a marker for stenosis. In this method, blood set flow and recirculation are compared between arterial and venous flow in the normal orientation, and then with reversed flow between the arterial and venous access sites, which are typically fistula needles which enter the vein. In the prior art, clinicians typically accomplished this by stopping the flow of blood, clamping all the lines, disconnecting the set or sets from the fistula needles, and then reconnecting the arterial line to the venous fistula while connecting the venous line to the arterial fistula. This of course is inconvenient and undesirable in that blood spillage and infection becomes a possibility. Accordingly, various other solutions relating to obtaining a reverse flow of blood in an extracorporeal blood circuit have been proposed, for example, Schnell, et al., U.S. Pat. Nos. 6,177,049 and 6,319,465, Krivitski, U.S. Pat. No. 6,308,737, Prosl, et al., U.S. Pat. No. 5,894,011 and Schneditz U.S. Pat. No. 5,830,365.

Also, regarding permanently implanted catheters, which are typically connected to larger veins or even the vena cava, it is known that catheter blockage may be relieved by reversing flow through the catheter and thus extending its useful life.

Accordingly, there are several reasons for why it is desirable to have an easily controlled flow reversal system in extracorporeal blood treatment.

By this invention, a flow reversal system is provided, free of slidably moving parts, and simply comprising connected flexible tubing, which has long been used in blood handling. The flow reversal system of this invention is quite inexpensive and easy to manufacture, utilizing generally conventional components, which have had long use, testing, and reliability, to obtain with ease the desired flow reversal when it is needed, with a minimal increase in the blood volume of the system because of the presence of the flow reversal apparatus, and generally free of stagnant flow areas.

DESCRIPTION OF THE INVENTION

By this invention, a tubular set portion is provided for circulating blood between a patient and an extracorporeal blood treatment device. This tubular set portion may be an integral part of joined arterial and venous blood flow sets, and/or fistula sets, which may otherwise be generally conventional in nature, apart from the improvement of this invention. Alternatively, the tubular set portion may be a separate set portion, which may be connected to any kind of conventional arterial and venous blood flow sets, and/or fistula sets and also connected to fistula needles, or percutaneous catheters to provide a complete flow circuit between the patient and an extracorporeal blood treatment device such as a dialyzer.

By this invention, the set portion comprises: an arterial tube for conveying blood from a patient toward the blood treatment device; a venous tube for conveying blood from the blood treatment device back toward the patient; and a pair of spaced, transverse tubes that each connect between the arterial tube and the venous tube. Each of the transverse tubes are capable of being sealed by a clamp (for clamp sealing by the usual collapse of a tube). Furthermore, the arterial and venous tubes are clamp sealable at a position between the spaced, transverse tubes.

Preferably, the wall-to-wall spacing between the transverse tubes is substantially equal to the wall-to-wall spacing of the arterial and venous tubes at a position between the transverse tubes. Furthermore, it is preferred for this wall-to-wall spacing, especially between the transverse tubes, to be so that both of the transverse tubes may be substantially completely sealed by the closure of one or two hemostat clamps or the like of a width to provide minimal residual blood volume left in the transverse tube. This is desirable since a significant residual blood volume in the clamped tubes may comprise a stagnant area for blood, as the blood flows through the arterial tube and the venous tube. Such stagnant areas for blood are likely to clot, which of course is undesirable. Such a substantially complete seal of a length of the transverse blood tubing as defined herein, or other blood tubing, is defined to comprise enough sealing closure of the tube to eliminate stagnant areas that can clot in normal operation.

Similarly, the wall-to-wall spacing between the sections of the arterial and venous tubes which are between the spaced, transverse tubes should be proportioned so that those sections of the arterial and venous tubes may be substantially completely sealed by the closure of the one or two hemostat clamps, or the like, to similarly provide a minimal residual blood volume, and essentially no clotting while at the same time not significantly collapsing the transverse tubes or other portions of the arterial and venous tubes.

Thus, a variable flow path maybe provided through the section which comprises the transverse tubes and adjacent arterial and venous tubes. The hemostat may close off the two transverse tubes in one flow position, causing blood flow to take place first through the arterial tube from the patient toward the blood treatment device, and then for the blood to pass through the venous tube away from the blood treatment device back toward the patient. However, when the hemostat closes off those portions of the arterial and venous tubes which are between the transverse tubes, the flow of the blood path is entirely different. The return blood from the treatment device passes from a first portion of the venous tube into a portion of the former arterial tube and then back to the patient. Flow from the arterial tube portion adjacent the device continues toward the blood treatment device, and draws blood from the former venous tube portion adjacent to the patient through the changed flow path, so that the flow in the arterial and venous tube portions adjacent to the patient is reversed, while the flow in the other arterial and venous tube portions spaced from the patient by the transverse tubes can remain constant, being typically driven by a roller pump.

Specifically, the distance between the spaced, transverse tubes, suitable for blood flows of about a hundred to a thousand ml./min., from wall to wall is preferably about 0.3 to 1.2 cm., while the corresponding spacing between the arterial and venous tubes is similarly about 0.3 to 1.2 cm. Stagnant areas may thus be avoided if the hemostat clamp or other clamp sealing member is of sufficient width to form a substantially complete seal of the entire lumen of each transverse tube in one instance, or the arterial and venous tubes between the spaced, transverse tubes in the other instance, to minimize stagnant areas for blood without significantly collapsing the tubes which are intended to be open. Specifically, the stagnant areas for blood adjacent to the clamp sealing member used should preferably comprise a total volume of no more than about one ml. for normal tubes of about 4–5 mm. inner diameter.

This maybe facilitated when the spaced, transverse tubes join the arterial and venous tubes with overall spacing to define a symmetrical structure having four flow paths extending therefrom, and where the flow paths are also generally of similar shape, to provide generally uniform pressure drop conditions in the respective alternative situations where (1) flow is blocked by clamp sealing in the transverse tubes and (2) flow is blocked by clamp sealing in the arterial and venous tubes between the spaced, transverse tubes. Typically, this symmetrical structure is in the form of a square.

The spaced, tubes form a quadrilateral figure, particularly a square but alternatively a rectangle, parallelogram, or rhombus, without crossing tubes.

Preferably, the set portion of this invention has arterial and venous tubes which each have a tube connector on each end, for respective connection with arteriovenous (AV) fistula needle sets and additional tube sets, for the completion of an overall tubular circuit system for the circulating of blood between a patient and an extracorporeal blood treatment device, such as a dialyzer. Preferably, in the case where the set portion of this invention is separate from the remainder of tubing sets that form the complete circuit, the arterial and venous tubes of the set portion each have a length of no more than about 100 cm. The tube connectors on the arterial and venous tubes may comprise luer type connections, which are a thoroughly tested and reliable type of connector, although other connectors may also be used.

Conventionally sized blood flow tubing may be used. Particularly, the inner diameter of the spaced, transverse tubes maybe about 1.5 to 10 mm. and their outer diameter maybe about 1 to 5 mm larger. Typically, pediatric tubes may have inner diameters of 1.5–4 mm; normal tubes may have inner diameters of 4–5 mm; and cardiovascular tubes may have inner diameters of 5–10 mm.

The arterial and venous tubes may have similar inner and outer diameters, especially at the positions extending between the spaced, transverse tubes.

Flow is controlled and reversed by the occlusion of two of the tubes which form a typically square array of tubes provided by the two spaced, transverse tubes and the arterial and venous tube portions to which they connect. For example, if both of the spaced, transverse tubes are closed with one or two hemostats, then blood flow proceeds normally, first through the arterial tube to reach the dialyzer, with the blood then passing through the dialyzer and back to the venous tube, through which it travels, and then is returned to the patient. However, if the arterial and venous tubes are clamped at their positions between the spaced, transverse tubes by one or more hemostats, then the blood flow, driven by a pump in the circuit, continues to pass blood in the normal way through the dialyzer, but the flow of blood in the tubes extending between the patient and the spaced, transverse tubes is reversed because of the change in the flow path.

This provides an extremely easy way, without any rotary valve or the like, to reverse the flow of blood into and out of the patient while maintaining the same blood flow direction through the extracorporeal blood treatment device. The direction of blood flow with respect to the patient can thus be easily controlled to flow in either direction, simply by proper manipulation of a hemostat or similar device.

DESCRIPTION OF SPECIFIC EMBODIMENTS

Figure 1:
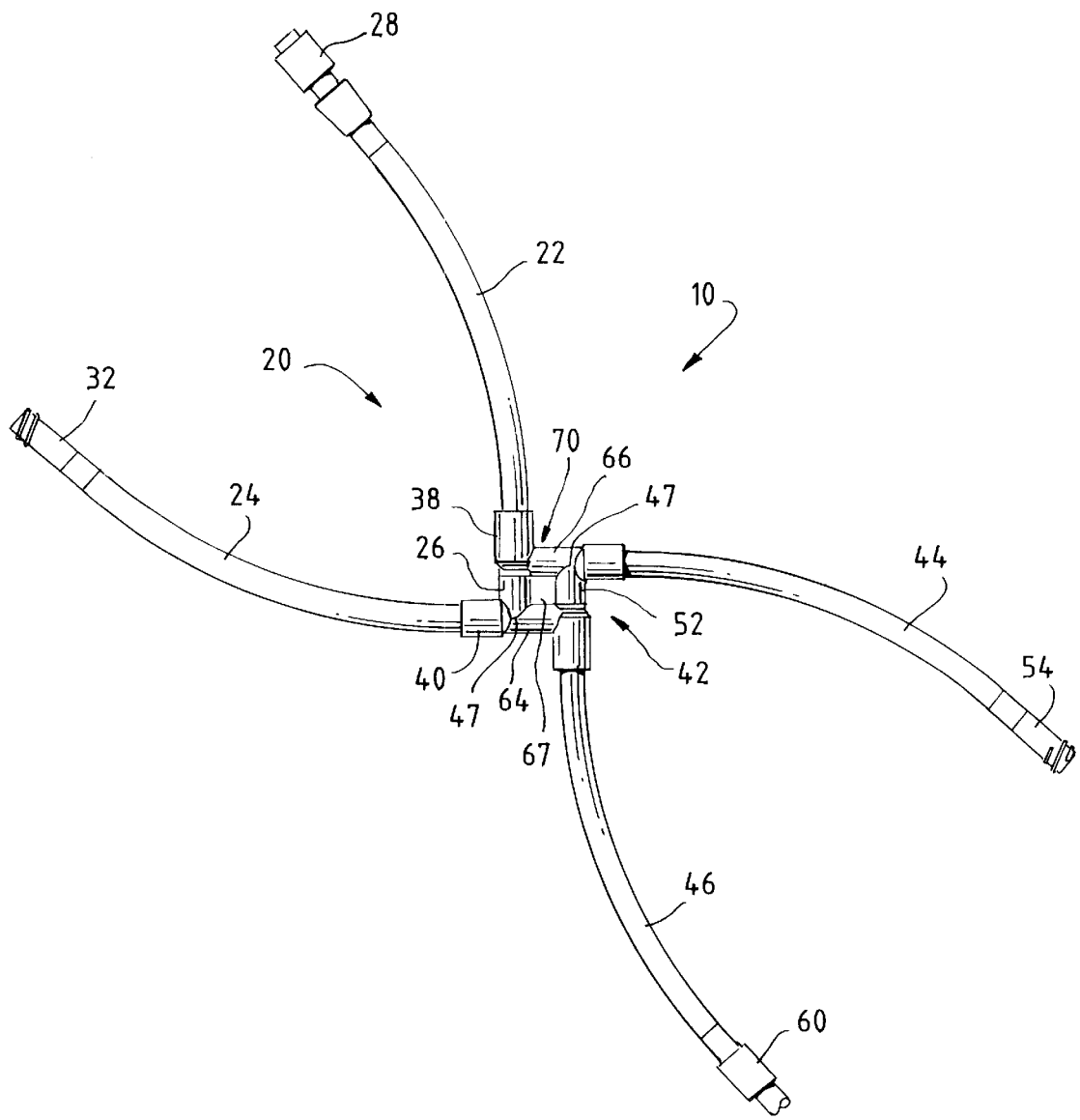
FIG. 1 is a plan view of a tubular set portion of this invention.
Figure 3:
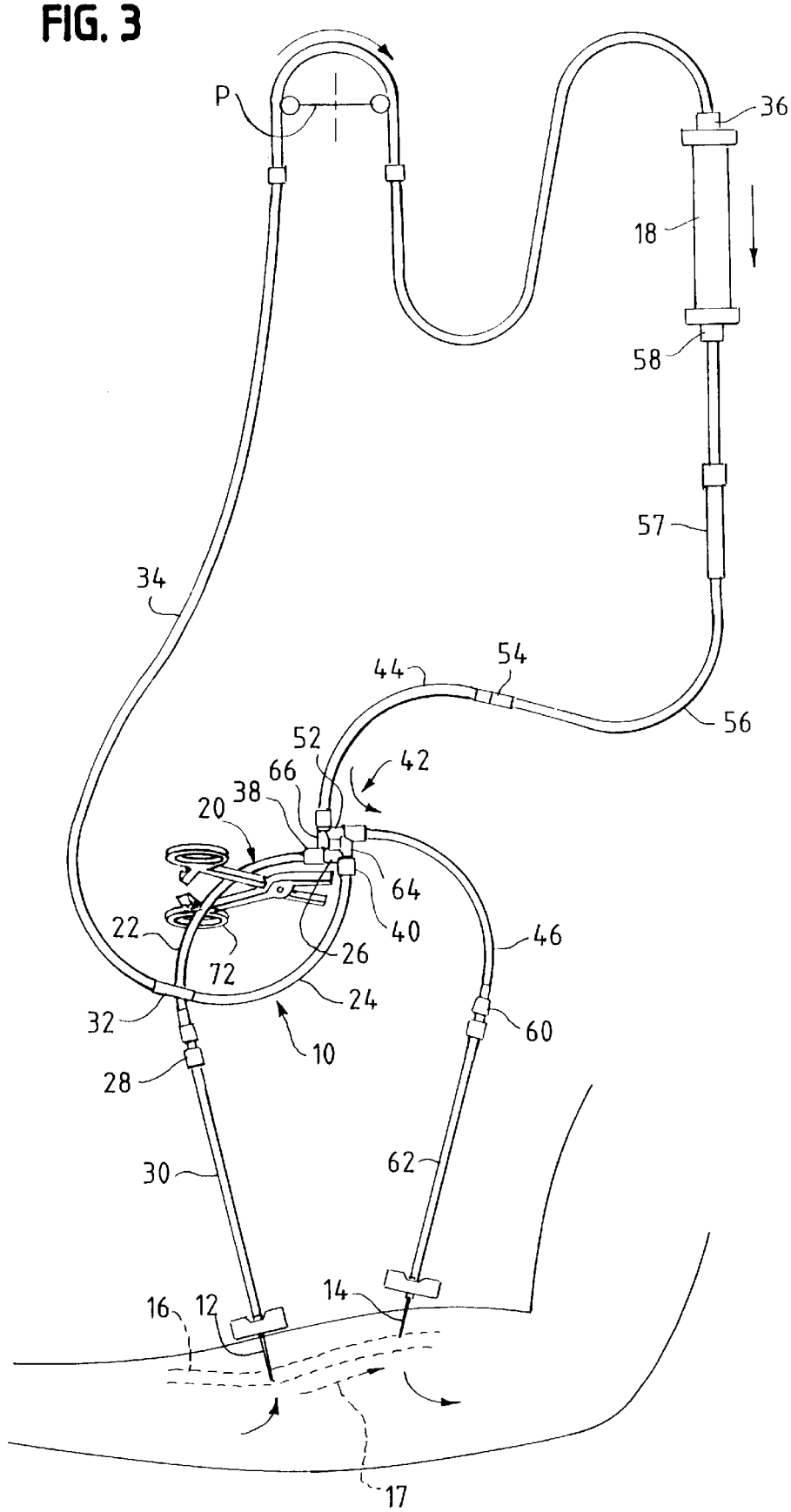
FIG. 3 is an elevational view of a dialysis blood flow circuit, showing the connection from patient to a dialyzer and back again, using the tubular set portion of FIG. 1.

Referring to the drawings, FIG. 1 shows a tubular set portion 10 in accordance with this invention. FIG. 3 shows set portion 10 connected to a pair of conventional cannula needles 12, 14, both connecting with a vein 16 of the patient, having a blood flow direction as indicated by arrow 17. Set portion 10 also may connect directly or indirectly, (but indirectly in this instance) with both ends of a dialyzer 18.

Tubular set portion 10 comprises an arterial tube 20 (FIG. 1) for conveying blood from a patient toward the blood treatment device, the arterial tube comprising two lengths 22, 24 of blood tubing, connected to a central tubing length 26. Tube portion 22 is a reversible flow portion, and has a connector 28, which may connect with a conventional cannula needle set 30, terminating in the cannula needle 12 itself, which is implanted in the patient to draw blood from vein 16. Arterial tube portion 24 carries a connector 32, which may connect directly to dialyzer 18, or, as here, connects to a conventional arterial tube set 34 which, in turn, connects with a blood inlet 36 of dialyzer 18. The respective tube portions 22, 24, are connected to central arterial tube portion 26 by tubular connectors 38, 40 to provide the complete arterial tube as normally used.

Venous tube 42 is similar, having tube portions 44, 46, connected by connectors 48, 50 (FIG. 1) to a short, central venous tube portion 52. Venous tube portion 44 has a connector 54 at its outer end, and is typically in connection with a conventional venous tube dialysis set 56 with bubble trap 57. Venous set 56, in turn, connects to the blood outlet 58 of dialyzer 18. Alternatively, venous tube portion 44 can connect directly with the dialyzer outlet 58. Tube portion 46 also carries a connector 60, which connects to fistula set 62 and its needle 14, which is embedded in the tissue and extending into vein 16. Portion 46 is a reversible flow tube portion.

Each of arterial tube 20 and venous tube 42 are each shown to have a right angled bend adjacent to the respective central tube lengths 26, 52. This provides equal flow conditions in all paths, whether normal or reversed.

Figure 2A:
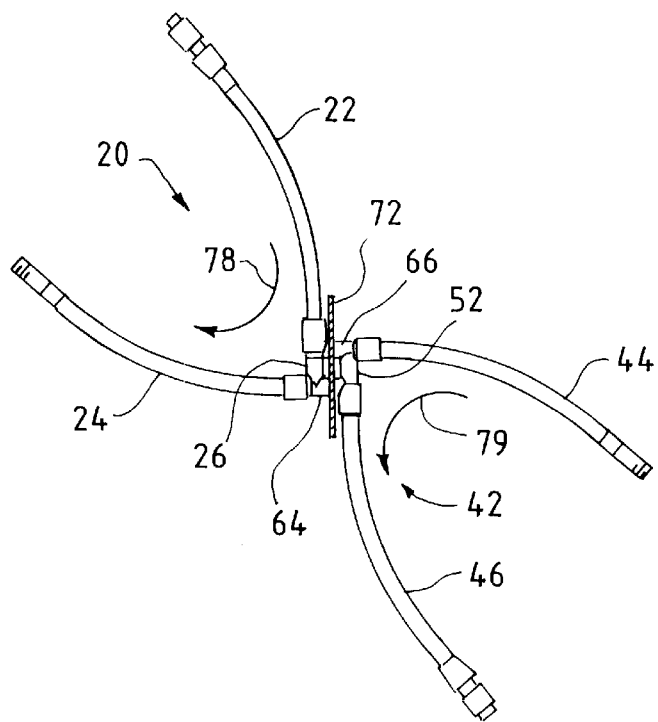
FIG. 2a is a perspective view of the tubular set portion of FIG. 1, showing it being clamped by a hemostat clamp to achieve normal flow.
Figure 2B:
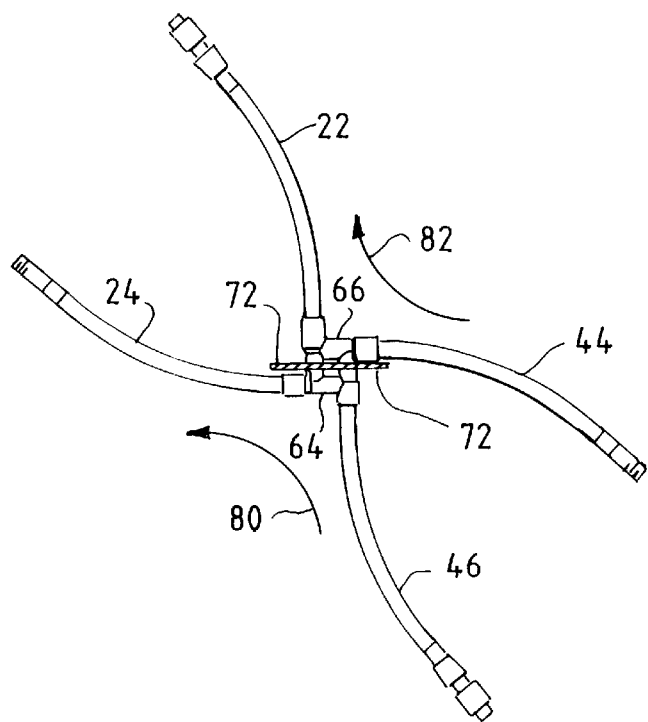
FIG. 2b is a view similar to FIG. 2a, showing a clamping configuration to achieve reverse flow.

In accordance with this invention, a pair of spaced, transverse tubes 64, 66 each interconnect with the respective arterial and venous tubes 20, 42. Transverse tubes 64, 66 may comprise telescoping tube portions extending from each of the arterial set portions 20, 42, being sealed together in telescoping relation after initial subassembly of the respective arterial and venous tube portions 20, 42, to provide the completed tubular set portion. Such tubular set portion thus has a central, substantially square array 70 (FIG. 1) of tubes comprising the central arterial and venous tube portions 26, 52, and the two transverse tubes 64, 66, positioned so that a conventional hemostat 72 can be used to pinch closed two opposite tubes of the four sets of tube portions in the square array 70. See. FIGS. 2a and 2b.

Specifically, in a first position, hemostat 72 may close spaced, transverse tubes 64, 66, (FIG. 2a) or, the same hemostat 72 may alternatively be used to close central tube portions 26, 52 (FIG. 2b). The resulting flow paths 78, 79, 80, 82 defined in these two different configurations flow in opposite flow directions from each other through the tube portions 22, 46, as pump P continues to push flow in a single direction in both cases through dialyzer 18 and tube portions 24, 44.

The four tube sections 26, 52, 64, 66 are joined together, defining a substantially square aperture 67 between them. The presence of such an aperture 67 reduces blood volume in the system, when compared with a flexible-walled chamber of similar size.

Specifically, when hemostat 72, or a solenoid clamp if desired, is closing transverse tubes 64, 66, a normal flow path for hemodialysis takes place, with blood being withdrawn through cannula set 30 (FIG. 3) and passing through the entire length of the arterial tube 20, comprising its tube sections 22, 26, 24, impelled by pump P through the optional, added arterial set 34, to enter dialyzer 18 through blood inlet port 36. The processed blood exits from blood outlet port 58 into typically a conventional venous set 56, which connects with venous tube 42, which comprises the venous tube portions 44, 52, and 46. The blood exits the venous tube of set portion 10 to pass into fistula set 62, to be returned to the vein 16. Typically, natural flow of the blood in vein 16 will be in the direction from cannula 12 to cannula 14.

When flow reversal in tubes 22, 46 is desired, hemostat 72 is removed, and replaced in a position to block central tubes 26 and 52. Due to the action of pump P, flow through the dialyzer 18 continues in the same direction. However, arterial tube 24, in that circumstance, draws blood from tube portion 46 which, in turn, is connected by fistula set 62 and fistula needle 14 to vein 16, so blood is withdrawn from the vein at the "downstream" position rather than the "upstream" position, as indicated by flow direction 17. Such blood passes through arterial set 34, dialyzer 18, and venous set 56, being forced by the pressure of pump P into tube portion 44. Blood from tube 44 passes through tube 66 into tube 22, from there passing into fistula set 30 and re-entering vein 16 through fistula needle 12. This provides a reverse flow at the patient side of the system, for purposes as described above, such as testing of fistula patency, or reversing flow in an implanted catheter, when such is used, to extend the useful life of the catheter even when there is a blockage of flow in the normal flow direction.

Alternatively, flow can be blocked without using a hemostat by tightly folding tube array 70 along the line defined by hemostat 72 in FIG. 2 and holding it there, to achieve a similar effect to a hemostat, thus providing normal flow. Also, tight folding of array 70 along the hemostat line 72 of FIG. 2b provides the reverse flow configuration.

It should be noted that the two tubes 22, 46 of the tubular set portion of this preferred embodiment, which connect with the patient through fistula sets 30, 62, are positioned as oblique opposites to each other, connecting in opposed corners of the square or rectangular tube array 70. Similarly, the two tubes 24, 44 that connect with the dialyzer or other extracorporeal device via sets 34, 56 connect in the square array at oblique, opposite corners 47, as shown.

The various short tubing sections 22, 24, 44, 46 may be flexible, and thus can be bent as needed for connection in their respective positions. The various tube sections 26, 52, 64, 66 are also flexible, so that they are easily collapsed and sealed by a hemostat or other pressure squeeze device, or folded with a sealing crease as described above.

It is preferred for the distance between the spaced, transverse tubes 64, 66 from outer wall to outer wall to be essentially 0.3 to 1.2 cm, to be not much larger than is necessary to receive a hemostat device 72 or other pressure squeeze instrument, to collapse the respective tubes 26, 52 for blood flow sealing without creating significant dead spaces of stagnancy in which blood can clot during operation, as shown in FIG. 2. Similarly, the central tube portions 26, 52 may be of a similar spacing from each other for the same reason: to allow collapse of tubes 64, 66 by hemostat without creating significant dead spaces.

Figure 4:
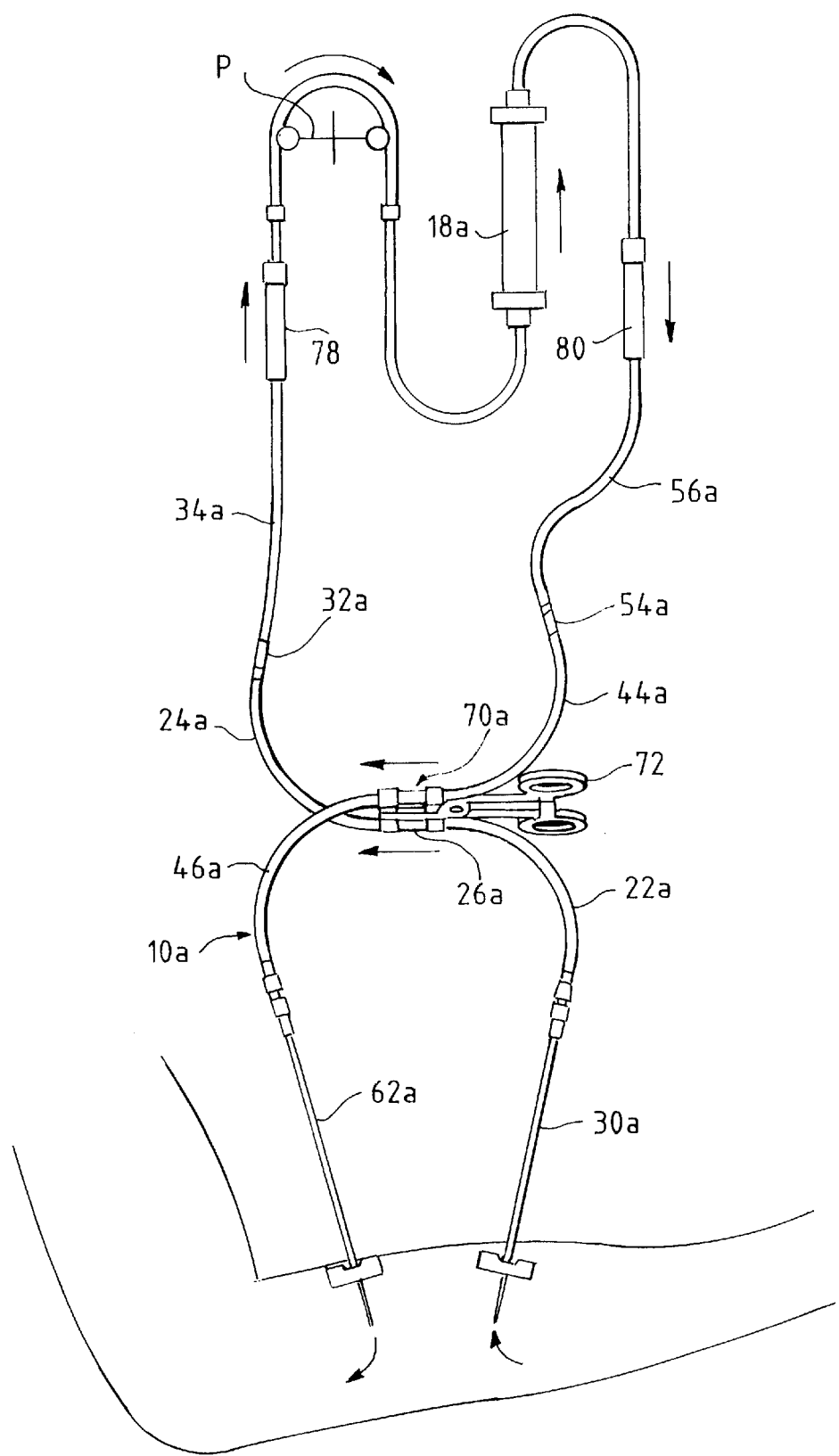
FIG. 4 is an elevational view of a dialysis blood flow circuit showing a slightly modified tubular set portion of this invention, with the spaced, transverse tubes being closed against flow by a hemostat, for a first flow of configuration of the system.
Figure 5:
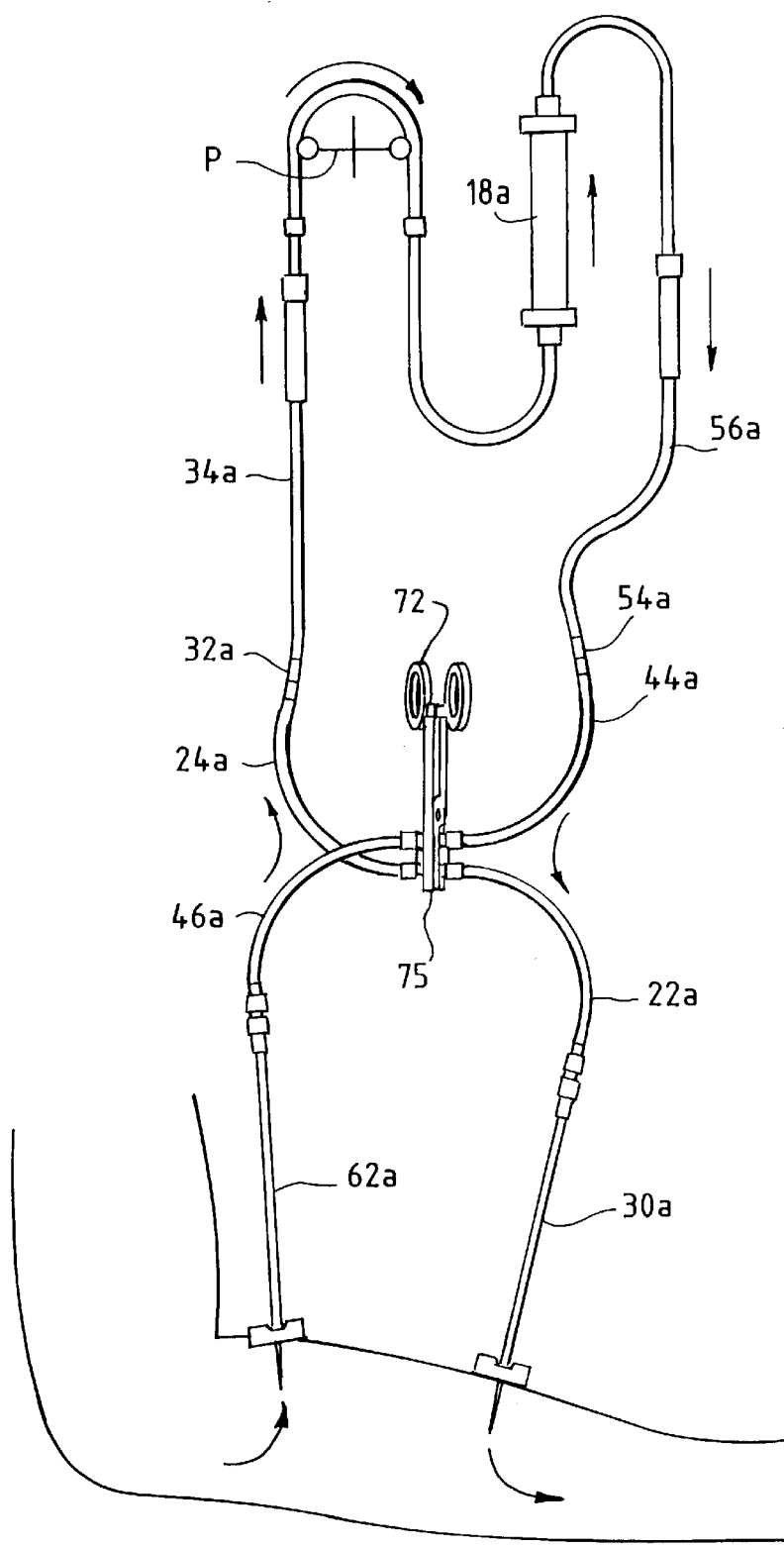
FIG. 5 is a plan view of the same system as is shown in FIG. 4, in which the hemostat is blocking flow through the portions of the arterial and venous tubes which are between the spaced, transverse tubes, to show a second flow configuration of the system.
Figure 6:
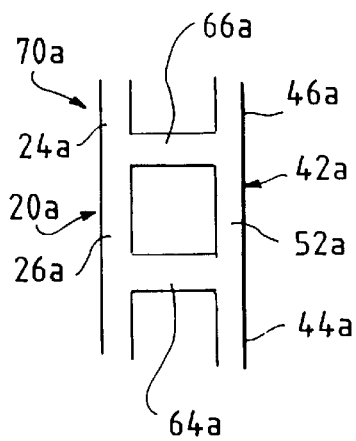
FIG. 6 is a fragmentary, schematic view of a portion of the blood flow circuit of FIGS. 4 and 5.

FIGS. 4 through 6 show another embodiment of the tubular set portion of this invention, in which the square array of tubes 70a has been modified from the corresponding square array 70 of the previous embodiment to normally provide straight flow through the respective arterial tube 20a and the venous tube 42a, and angled flow in the other flow mode, but is otherwise similar structure and function to the previous arterial tube 20 and venous tube 42. This is particularly schematically illustrated in FIG. 6, with the spaced transverse tubes 64a, 66a being also shown. The difference can be best seen by a contrast of the two embodiments of FIG. 1 and FIG. 6.

FIG. 4 shows a blood dialysis circuit operating in its normal flow mode with a set portion comprising square array of tubes 70a and otherwise similar to the previous embodiment, having dialyzer 18a, venous supplemental set portion 56a, which connects through connector 54a to venous tubing portion 44a. Blood flow then passes in straight-flow manner through square array 70a to a second, reversible flow tube portion 46a of the venous tubing and thence back to the patient by way of fistula set 62a. Blood is drawn from the patient through arterial fistula set 30a, passing into the arterial tubing described above, comprising reversible flow tube portion 22a and arterial tubing portion 24a which connect in straight flow relation through square array 70a, and connect with supplemental arterial tubing 34a to flow past roller pump P into dialyzer 18a. Arterial and venous bubble trap chambers 78, 80 may provided as desired.

Flow through spaced, transverse tubes 64a, 66a is shut off by hemostat 72, as in the previous embodiment.

In FIG. 5, the same tubular array as FIG. 4 is modified by a shifting of hemostat 72 to its other clamping position and flow mode, where the portions 26a, 52a of the respective arterial and venous tubes 20a, 42a which lie between transverse tubes 64a, 66a are clamped. The width of the jaws 75 of hemostat 72 are proportioned to clamp and substantially completely seal essentially the full length of tube sections 26a, 52a so that there is little or no dead space for stagnant blood to collect, without significant interference with the flow of blood through transverse tubes 64a, 66a (Similarly, in the FIG. 4 configuration, tubes 64a, 66a are likewise clamped by jaws 75 of a width to substantially completely seal and eliminate dead space without interference of flow through tube sections 26a, 52a).

In the circumstances of FIG. 5, the blood flow through fistula sets 30a, 62a is reversed, while the blood flow through tube sections 24a, 44a continues in its usual flow direction, as impelled by pump P. The flow path in this instance is through reversible flow tube portion 46a, which connects through section 66a to arterial tube portion 24a so that the flow continues on normally to dialyzer 18a. The blood flow returns to venous tube 44a, and is transferred through transverse tube 64a to arterial tube portion 22a, to be returned to the patient in reverse flow manner through fistula set 30a.

Connector 32a provides connection with the added arterial set portion 34a, and connector 54a connects with added venous set portion 56a.

When the set portion 10 (or 10a) is in a separate form, as shown in FIG. 1, with connectors on each outer end for connection with other tubing portions, it is generally preferred that each of the arterial and venous tubes 20, 42 have an overall length of no more than about 100 cm.

To summarize, referring to FIG. 2a in light of the previous drawings, normal flow is achieved when hemostat 72 is blocking flow through transverse tubes 64, 66, as indicated by the respective flow arrows 78, 79 for the flow through the arterial tube 20 and venous tube 42. Then, in FIG. 2b, the position of clamp 72 is placed to block flow through tubes 26, 52 and to permit flow through tubes 64, 66, resulting in reverse flow paths 80, 82, as previously described.

Thus, a set portion is provided, optionally for use with conventional arterial and venous sets to provide the capability of flow reversal for improved extracorporeal blood handling at the flow portions adjacent to the patient, with a generally constant direction of flow through the tubing set in the vicinity of the dialyzer or other blood treatment device. This is accomplished using only tube components, which may be dimensioned so that stagnant areas where blood can collect may be essentially eliminated, and there is little increase in the blood volume of the set in use that is attributable to the flow reversing member 70.

The above has been offered for illustrative purposes only, and is not intended to limit the scope of the invention of this application, which is as defined in the claims below.

That which is claimed is:

1. A tubular set portion for circulating blood between a patient and an extracorporeal blood treatment device, which set portion comprises:

an arterial tube for conveying blood from a patient toward the blood treatment device;

a venous tube for conveying blood from the blood treatment device back toward the patient; and a pair of spaced, transverse tubes that each connect between the arterial tube and the venous tube, each of said transverse tubes being capable of clamp sealing, said arterial and venous tubes having clamp sealable tube portions between said spaced, transverse tubes, said spaced, transverse tubes and tube portions forming a quadrilateral figure.

2. The tubular set portion of claim 1 in which the spaced, transverse tubes join the arterial and venous tubes with a spacing to form substantially a square.

3. The set portion of claim 1 in which the distance between the spaced, transverse tubes from wall-to-wall is essentially 0.3 to 1.2 cm.

4. The set portion of claim 1 in which the wall-to-wall distance between the arterial and venous tubes between said spaced, transverse tubes is essentially 0.3 to 1.2 cm.

5. The set of claim 4 in which the distance between the spaced, transverse tubes from wall to wall is essentially 0.3 to 1.2 cm.

6. The set portion of claim 1 in which said arterial and venous tubes have a tube connector on each end, for respective connection with A.V. fistula needle sets and additional tube sets for the circulating of blood between a patient and an extracorporeal blood treatment device.

7. The set portion of claim 6 in which said tube connector is a luer-type connector.

8. The set portion of claim 6 in which said arterial and venous tubes each have a length of no more than 100 cm.

9. The set portion of claim 1 in which the wall-to-wall distance respectively between said arterial and venous tubes, and between the spaced, transverse tubes, is essentially 0.3 to 1.2 cm, said spaced transverse tubes joining the arterial and venous tubes with a spacing to form substantially a square aperture between them.

10. The set portion of claim 9 in which said arterial and venous tubes have a tube connector on each end, for respective connection with I.V. fistula needle sets and additional tube sets for the circulating of blood between a patient and an extracorporeal blood treatment device.

11. The set portion of claim 10 in which each tube connector is a luer-type connector.

12. The set portion of claim 10 in which said arterial and venous tubes each have a length of no more than 100 cm.

13. The tubular set portion of claim 1 in which the spaced, transverse tubes join the arterial and venous tubes with overall spacing to define a symmetrical structure having four flow paths extending therefrom, to provide generally uniform pressure drop conditions in the respective alternative situations where (1) flow is blocked by clamp sealing of the transverse tubes and (2) flow is blocked by clamp sealing of the arterial and venous tubes between the spaced, transverse tubes.

14. The tubular set portion of claim 13 in which the spaced, transverse tubes join the arterial and venous tubes with a spacing to form substantially a square.

15. The tubular set portion of claim 13 in which said spaced, transverse tubes are clamp sealed by a clamp sealing member, said clamp sealing member being of sufficient width to substantially completely seal the lumen of each transverse tube, to minimize stagnant areas for blood in said transverse tubes without significantly collapsing said arterial and venous tubes.

16. The tubular set portion of claim 15 in which said stagnant areas for blood in said transverse tubes comprise a total volume of no more than about one ml.

17. The tubular set portion of claim 13 in which said arterial and venous tubes between the spaced transverse tubes are clamp sealed by a clamp sealing member, said clamp sealing member being of sufficient width to substantially completely seal the lumen of each of said arterial and venous tubes between the spaced, transverse tubes to minimize stagnant areas for blood in said arterial and venous tubes between the spaced transverse tubes, without significantly collapsing said spaced, transverse tubes.

18. The tubular set portion of claim 17 of which said stagnant areas for blood in said transverse tubes comprise a total volume of no more than about one ml.

19. A tubular set portion for circulating blood between a patient and an extracorporeal blood treatment device, which set portion comprises;
    an arterial tube for conveying blood from a patient toward the blood treatment device;
    a venous tube for conveying blood from the blood treatment device back toward the patient; and
    a pair of spaced, transverse tubes that each connect between the arterial tube and the venous tube, each of said transverse tubes being capable of clamp sealing, said arterial and venous tubes being capable of clamp sealing between said spaced, transverse tubes, said, spaced, transverse tubes joining the arterial and venous tubes with overall spacing to define a square structure and having four flow paths extending therefrom, to provide generally uniform pressure drop conditions in the respective alternative situations where (1) flow is blocked by clamp sealing in the transverse tubes and (2) flow is blocked by clamp sealing in the arterial and venous tubes between the spaced, transverse tubes.

20. The tubular set portion of claim 19 in which said spaced, transverse tubes are clamp sealed by a clamp sealing member, said clamp sealing member being of sufficient width to substantially collapse the entire lumen of each transverse tube, to minimize stagnant areas for blood in said transverse tubes without significantly collapsing said arterial and venous tubes.

21. The tubular set portion of claim 20 in which said stagnant areas for blood in said transverse tubes comprise a total volume of no more than about one ml.

22. The tubular set portion of claim 21 in which the distance between the spaced, transverse tubes, and the distance between said arterial and venous tubes between the spaced, transverse tubes, measured from wall to wall, is essentially 0.3 to 1.2 cm.

23. The tubular set portion of claim 19 in which said arterial and venous tubes between the spaced, transverse tubes are clamp sealed by a clamp sealing member, said clamp sealing member being of sufficient width to substantially collapse the entire lumen of each of said arterial and venous tubes between the spaced transverse tubes, to minimize stagnant areas for blood in said transverse tubes without significantly collapsing the remainder of said transverse tubes.

24. The tubular set portion of claim 23 in which said stagnant areas for blood in said arterial and venous tubes between the spaced, transverse tubes comprise a total volume of no more than about 1.5 ml.

25. The tubular set portion of claim 24 in which the distance between the spaced, transverse tubes, and the distance between the arterial and venous tubes between said spaced, transverse tubes, measured from wall to wall, is each essentially 0.3 to 1.2 cm.

26. The set portion of claim 19 in which said arterial and venous tubes have a tube connector on each end, for respective connection with IV fistula needle sets and additional tube sets for the circulating of blood between a patient and an extracorporeal blood treatment device.

27. The set portion of claim 26 in which said arterial and venous tubes each have a length of no more than 100 cm.

28. The tubular set portion of claim 1 in which said spaced, transverse tubes are clamp sealed by a clamp sealing member, said clamp sealing member being of sufficient width to substantially completely seal the lumen of each transverse tube, to minimize stagnant areas for blood in said transverse tubes, without significantly collapsing said arterial and venous tubes.

29. The tubular set portion of claim 28 in which said stagnant areas for blood in said transverse tubes comprise a total volume of no more than about one ml.

30. The tubular set portion of claim 1 in which said arterial and venous tubes between the spaced transverse tubes are clamp sealed by a clamp sealing member, said clamp sealing member being of sufficient width to substantially completely seal the lumen of each of said arterial and venous tubes between the spaced, transverse tubes to minimize stagnant areas for blood in said arterial and venous tubes between the spaced transverse tubes, without significantly collapsing said spaced, transverse tubes.

31. The tubular set portion of claim 30 in which said stagnant areas for blood in said transverse tubes comprise a total volume of no more than about one ml.

32. A tubular set portion for circulating blood between a patient and an extracorporeal blood treatment device, which set portion comprises
    an arterial tube for conveying blood from a patient toward the blood treatment device;
    a venous tube for conveying blood from the blood treatment device back toward the patient; and
    a pair of spaced, transverse tubes that each connect between the arterial tube and the venous tube, each of said tubes being capable of clamp sealing, said arterial and venous tubes having clamp sealable tube portions between said spaced transverse tubes, in which the spaced, transverse tubes join the arterial and venous tubes with overall spacing to define a symmetrical structure and having four flow paths extending therefrom, to provide generally uniform pressure conditions in the respective alternative situations where (1)

flow is blocked by clamp sealing of the transverse tubes, and (2) flow is blocked by clamp sealing of the arterial and venous tubes between the spaced transverse tubes.

33. The tubular set portion of claim 32 in which each of the four flow paths each define a single, angled turn.

34. A tubular set portion for circulating blood between a patient and an extracorporeal blood treatment device, which set portion comprises;

an arterial tube for conveying blood from a patient toward the blood treatment device;

a venous tube for conveying blood from the blood treatment device back toward the patient; and a pair of spaced, transverse tubes that each connect between the arterial tube and the venous tube, each of said transverse tubes being capable of clamp sealing, said arterial and venous tubes having clamp sealable tube portions between said spaced, transverse tubes, in which said spaced, transverse tubes are clamp sealed by a clamp sealing member, said clamp sealing member being of sufficient width to substantially completely seal the lumen of each transverse tube, to minimize stagnant areas for blood in said transverse tubes without significantly collapsing said arterial and venous tubes.

35. A tubular set portion for circulating blood between a patient and an extra corporeal blood treatment device, which said portion comprises:

an arterial tube from conveying blood from a patient toward the blood treatment device;

a venous tube for conveying blood from the blood treatment device back toward the patient; and a pair of spaced, transverse tubes that each connect between the arterial tube and the venous tube, each of said transverse tubes being capable of clamp sealing, said arterial and venous tubes having clamp sealable tube portions between said spaced, transverse tubes, in which the arterial and venous tubes between the spaced transverse tubes are clamp sealed by a clamp sealing member, said clamp sealing member being of sufficient width to substantially completely seal the lumen of each of said arterial and venous tubes between the spaced, transverse tubes to minimize stagnant areas for blood in said arterial and venous tubes between the spaced, transverse tubes without significantly collapsing said spaced transverse tubes.

36. The method of circulating blood between a patient and an extracorporeal treatment device, using a set portion which comprises; an arterial tube for conveying blood for a patient toward the blood treatment device, a venous tube for conveying blood from said blood treatment device back toward the patient, and spaced, transverse tubes that each connect with the arterial tube and the venous tube, each of said tubes being capable of clamp sealing, said arterial and venous tubes having clamp sealable tube portions between said spaced, transverse tubes, further in which said spaced, transverse tubes and tube portions form a quadrilateral figure, said method comprising the steps of clamp sealing the spaced, transverse tubes by a clamp sealing member, said clamp sealing member being of sufficient width to substantially completely seal the lumen of each transverse tube without significantly collapsing said arterial and venous tubes; and passing blood to said arterial set from the patient and then to the blood treatment device, and passing said blood back from the blood treatment device through said venous set to the patient.

37. The method of claim 36 which further comprises the step of removing said clamp sealing of said transverse tubes and clamp sealing the arterial and venous tubes between the spaced, transverse tubes with a clamp sealing member, said clamp sealing member being of sufficient width to substantially completely seal the lumen of each of said arterial and venous tubes between the spaced, transverse tubes without significantly collapsing the spaced transverse tubes, and thereafter;

passing blood from said patient through said arterial tube, said extracorporeal blood treatment device, and said venous tube back to the patient, in which the direction of flow of said blood in portions of said arterial and venous tubes positioned between said quadrilateral figure and the extracorporeal blood treatment device is unchanged, and the direction of blood flow through arterial and venous tube portions positioned between the quadrilateral figure and the patient is reversed in direction.

38. The method of claim 37 in which respective sections of said arterial and venous tubes have ends which each connect with a fistula tubing and fistula needles which are in connection with the vascular system of the patient, the respective arterial and venous tube sections connecting with the quadrilateral figure at positions which are spaced from each other by the connections of the remaining sections of the arterial and venous tubes.

* * * * *